(12) United States Patent
Hu et al.

(10) Patent No.: US 11,337,972 B2
(45) Date of Patent: *May 24, 2022

(54) PHARMACEUTICAL PREPARATION AND USE THEREOF

(71) Applicant: WUHAN LL SCIENCE AND TECHNOLOGY DEVELOPMENT CO., LTD., Hubei (CN)

(72) Inventors: Xiaojing Hu, Hubei (CN); Lina Qian, Hubei (CN); Zhichao Zhang, Hubei (CN); Yuanping Wang, Hubei (CN); Yongkai Chen, Hubei (CN); Wei Feng, Hubei (CN); Wenwen Qi, Hubei (CN); Chaodong Wang, Hubei (CN)

(73) Assignees: WUHAN LL SCIENCE AND TECHNOLOGY DEVELOPMENT CO., LTD., Hubei (CN); WUHAN QR PHARMACEUTICALS CO., LTD., Hubei (CN); WUHAN ZY PHARMACEUTICALS CO., LTD., Hubei (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/979,305

(22) PCT Filed: Mar. 8, 2019

(86) PCT No.: PCT/CN2019/077449
§ 371 (c)(1),
(2) Date: Sep. 9, 2020

(87) PCT Pub. No.: WO2019/170136
PCT Pub. Date: Sep. 12, 2019

(65) Prior Publication Data
US 2021/0052579 A1    Feb. 25, 2021

(30) Foreign Application Priority Data

Mar. 9, 2018    (CN) .......................... 201810195617.1

(51) Int. Cl.
| | | |
|---|---|---|
| *A61K 31/497* | (2006.01) | |
| *A61K 31/216* | (2006.01) | |
| *A61K 47/38* | (2006.01) | |
| *A61K 47/32* | (2006.01) | |
| *A61K 47/12* | (2006.01) | |
| *A61K 47/02* | (2006.01) | |
| *A61K 47/26* | (2006.01) | |

(52) U.S. Cl.
CPC .......... *A61K 31/497* (2013.01); *A61K 31/216* (2013.01); *A61K 47/02* (2013.01); *A61K 47/12* (2013.01); *A61K 47/26* (2013.01); *A61K 47/32* (2013.01); *A61K 47/38* (2013.01)

(58) Field of Classification Search
CPC ........ A61K 31/41; A61K 47/38; A61K 47/12; A61K 47/32; A61K 31/216; A61K 31/497; A61K 31/4245; A61K 47/26; A61K 9/2059; A61K 47/02; A61K 2300/00; A61P 9/00
See application file for complete search history.

(56) References Cited

U.S. PATENT DOCUMENTS

2005/0187269 A1*  8/2005  Kuroita ............... A61P 9/10
                                                    514/364
2018/0140579 A1*  5/2018  Albrecht ............... A61K 31/41

FOREIGN PATENT DOCUMENTS

| CN | 1615134 A | 5/2005 |
|---|---|---|
| CN | 103709154 A | 4/2014 |

(Continued)

OTHER PUBLICATIONS

Ettmayer et al., "Lessons learned from Market and investigational Prodrugs," Journal of Medicinal of Chemistry, 2004, vol. 47, 2394. (Year: 2004).*

(Continued)

*Primary Examiner* — Jianfeng Song
(74) *Attorney, Agent, or Firm* — Novick, Kim & Lee, PLLC; Allen Xue

(57) ABSTRACT

A pharmaceutical preparation includes a first active component, a second active component and pharmaceutically acceptable excipients. The first active component is at least one selected from the group consisting of a neutral endopeptidase inhibitor and a precursor, an active metabolite, a stereoisomer, a pharmaceutically acceptable salt, a prodrug and a solvate thereof. The second active component is at least one selected from the group consisting of a compound represented by the following formula (I) or a precursor, an active metabolite, a stereoisomer, a pharmaceutically acceptable salt, a prodrug and a solvate thereof. The pharmaceutically acceptable excipients include one or more disintegrants and/or one or more fillers.

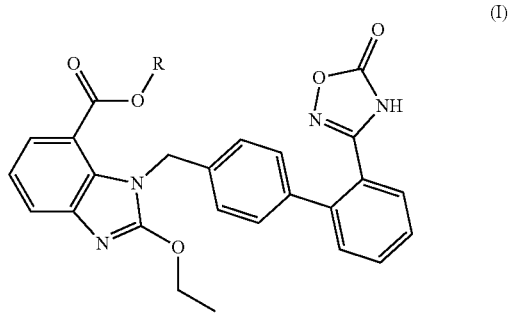

11 Claims, No Drawings

(56) References Cited

FOREIGN PATENT DOCUMENTS

| | | | | |
|---|---|---|---|---|
| CN | 104774196 | * | 7/2015 | |
| CN | 105693543 A | | 6/2016 | |
| WO | WO-9213564 A1 | * | 8/1992 | ........... A61K 38/556 |

OTHER PUBLICATIONS

Vining, "Functions of Secondary Metabolites", Annu. Rev. Microbiol. Oct. 1990, vol. 44, p. 406. (Year: 1990).*
Vippagunta et al. "Crystalline Solids,"Advanced Drug Delivery Reviews, 2001, 48, pp. 18. (Year: 2001).*
Müller, Inorganic Chemistry, p. 14-15, 1993. (Year: 1993).*

\* cited by examiner

PHARMACEUTICAL PREPARATION AND USE THEREOF

This application is an U.S. national stage application of PCT International Application No. PCT/CN2019/077449, filed Mar. 8, 2019, which claims the priority of Chinese application No. 201810195617.1 submitted to China National Intellectual Property Administration on Mar. 9, 2018, which is entitled "Pharmaceutical preparation and use thereof." The earlier application is hereby incorporated by reference in its entirety.

FIELD OF THE INVENTION

The invention relates to the field of pharmaceutical preparations, specifically relates to a pharmaceutical preparation and use thereof.

BACKGROUND

Cardiovascular diseases, also known as circulatory disease, refer to a series of diseases that affect the circulatory system. The circulatory system mainly includes the heart and the blood vessels (arteries, veins, microvessels). According to statistics, cardiovascular diseases are the leading cause of death globally, and people dying annually from cardiovascular diseases are more than from any other causes. Common cardiovascular diseases include: hypertension, heart failure, coronary heart disease, heart disease, atherosclerosis, angina, left ventricular dysfunction, hypertrophic cardiomyopathy, diabetic cardiomyopathy, supraventricular and ventricular arrhythmias, atrial fibrillation, cardiac fibrosis, atrial flutter, detrimental vascular remodeling, myocardial infarction and sequelae thereof, etc. The cardiovascular diseases usually have similar etiology, pathological processes and treatment schedules. Most cardiovascular diseases can be prevented by addressing risk factors such as tobacco use, unhealthy diet, obesity, hypertension, diabetes and hyperlipidemia.

The World Health Organization believes that the recurrence of cardiovascular disease or the risk of cardiovascular death can be significantly reduced by pharmaceutical combinations, for example the combination of cholesterol-lowering statins, antihypertensive drugs and aspirin. However, the arbitrary combination of drugs having different mechanisms for the treatment of cardiovascular diseases may not necessarily achieve advantageous effects. Therefore, the development of pharmaceutical compositions that show combined treatment effect may provide more effective prevention and treatment of cardiovascular diseases.

Neutral endopeptidase (NEP) is a zinc metallopeptidase located on the surface of endothelial cells. The inhibition of NEP can increase the levels of atrial natriuretic peptide (ANP), brain natriuretic peptide (BNP), C-type natriuretic peptide (CNP), bradykinin, and adrenomedullin. Accordingly, in pathological states, NEP inhibitors can play a role in diuresis, vasodilatation, improving endothelial function, and inhibiting vascular smooth muscle cell proliferation, thereby improving vascular hemodynamics, preventing the formation of atherosclerosis, and slowing the progression of heart failure.

Angiotensin II (Ang II) is an important regulatory factor for maintaining the dynamic equilibrium of the body fluid in the body, involving the equilibrium of blood pressure, electrolyte, etc. A large number of literatures have shown that Ang II plays a major role in the pathogenesis of hypertension, arterial diseases, cardiac hypertrophy, heart failure, diabetes, nephropathy and the like. As the abnormally and persistently increased level of Ang II is directly related to the occurrence and development of hypertension, cardiac hypertrophy, heart failure and the like, blocking the binding of Ang II to the specific receptors thereof can exert protective effects on cardiovascular and cerebrovascular systems. The effects of Angiotensin II Receptor Blockers (ARBs) on reduction of cardiovascular disease mortality and morbidity have been demonstrated in many randomized clinical trials, and ARB drugs are widely used abroad for the prevention and treatment of hypertension and other heart and kidney diseases. ARBs currently used in the clinical can be divided into two categories according to their structures: (1) biphenyltetrazoles, including losartan, valsartan, irbesartan, candesartan cilexetil and azilsartan medoxomil; and (2) non-biphenyltetrazoles, including eprosartan and telmisartan.

Chinese patent application CN1615134A discloses pharmaceutical compositions containing valsartan or pharmaceutically acceptable salts thereof, and NEP inhibitor or pharmaceutically acceptable salts thereof; Chinese patent application CN105693543A discloses pharmaceutical compositions containing salts of NEP inhibitor sacubitril (AHU 377, CAS No. 149709-62-6) and pharmaceutical excipients, and AT1 receptor antagonists, such as losartan, eprosartan, valsartan, irbesartan, or pharmaceutically acceptable salts thereof; and Chinese patent application CN105837464A also discloses pharmaceutical compositions containing NEP inhibitor sodium sacubitril and pharmaceutical excipients, and other active ingredients, such as losartan, eprosartan, valsartan, irbesartan, or pharmaceutically acceptable salts thereof.

Chinese patent application CN103709154A discloses a compound represented by the following formula (I) for the first time:

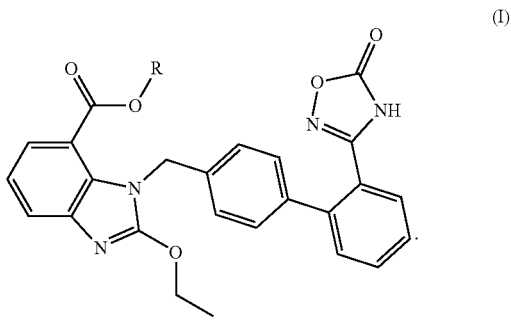

The above-mentioned compound, a sartan drug coupled with ligustrazine or a NO donor, is a prodrug of the angiotensin II receptor antagonist azilsartan (TAK-536). The compound releases hydroxyligustrazine or NO in vivo, which interacts synergistically with azilsartan and enhances the antihypertensive effect, produces a certain heart rate lowering effect, reduces side effects, and also shows a more ideal protective effect on the heart and kidney of patients. In further studies, the inventors found that the potassium salt of the compound of formula (I), i.e., the following compound of formula (II), has higher solubility, higher bioavailability, more stronger and longer-lasting antihypertensive effect, more obvious and longer-lasting heart rate lowering effect, higher safety, better protective effect on the heart and kidney functions of patients, and thus can be used for the prevention and/or treatment of hypertension, chronic heart failure, diabetic nephropathy and the like,

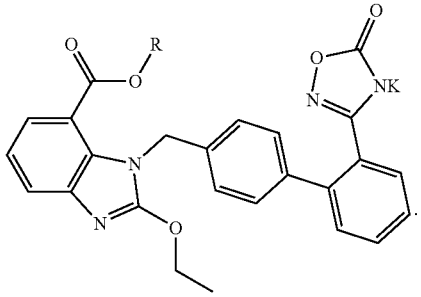
(II)

To improve the stability and drug-forming properties of the compound, the inventors conducted further formulation studies and found that the compound of formula (I) was highly hygroscopic and became viscous after absorbing moisture, and could not be effectively disintegrated, resulting in poor dissolution and release performances of the active ingredient. In further studies, the inventors found that the drug combination of the neutral endopeptidase inhibitor and the compound of formula (I) was highly hygroscopic when exposed to water and became viscous after absorbing moisture, which could not be effectively disintegrated, causing poor dissolution and release performances of the active ingredients.

SUMMARY OF THE INVENTION

To solve the above-mentioned technical problem, the invention provides a pharmaceutical preparation comprising a first active component, a second active component and pharmaceutically acceptable excipients; wherein, the first active component is at least one selected from the group consisting of a neutral endopeptidase inhibitor and a precursor, an active metabolite, a stereoisomer, pharmaceutically acceptable salt, prodrug and solvate thereof;

the second active component is at least one selected from the group consisting of a compound represented by the following formula (I) or a precursor, an active metabolite, a stereoisomer, pharmaceutically acceptable salt, prodrug and solvate thereof;

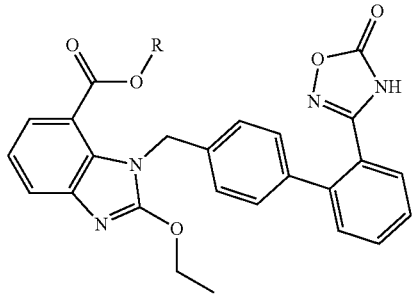
(I)

wherein, R represents

each a is identical or different, and is independently selected from 0, 1, 2, 3, 4, 5 or 6;

$R_1$ represents a substituted or unsubstituted group as follows: $C_1$-$C_8$ alkyl, $C_2$-$C_8$ alkenyl, $C_2$-$C_8$ alkynyl,

$(CH_2)_nO(CH_2)_m$, aryl, or heteroaryl; wherein $C_b$ and $C_c$ in

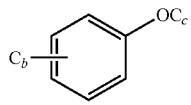

represent an alkyl group containing b or c carbon atoms, respectively; b and c are identical or different, and are independently selected from 0, 1, 2, 3, 4, 5 or 6; and wherein n and m in $(CH_2)_nO(CH_2)_m$ are identical or different, and are independently selected from 1, 2, 3, 4, 5 or 6;

$R_2$ represents H, halogen, nitro, cyano, or a substituted or unsubstituted group as follows: $C_1$-$C_8$ alkoxy, $C_1$-$C_8$ alkyl, $C_1$-$C_8$ alkylsulfonylamino, arylsulfonylamino, heteroarylsulfonylamino, aminosulfonyl, amino;

$R_3$ does not exist, or represents a substituted or unsubstituted group as follows: $C_1$-$C_8$ alkyl, $C_1$-$C_8$ alkoxy, $C_2$-$C_8$ alkenyloxy, $C_2$-$C_8$ alkynyloxy, $C_1$-$C_6$ alkoxy-$C_1$-$C_6$ alkyl,

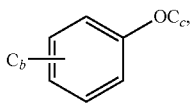

aryl, heteroaryl, wherein b and c in

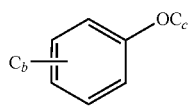

represent the numbers of carbon atoms in the alkyl chain, and are independently selected from 0, 1, 2, 3, 4, 5 or 6;

$R_4$ represents cyano, or a substituted or unsubstituted group as follows: aryl, arylsulfonyl, heteroaryl, $C_1$-$C_8$ alkoxy, $C_1$-$C_8$ nitrate (—$C_1$-$C_8$ alkyl-$ONO_2$), $C_1$-$C_8$ alkyl;

$R_5$ represents cyano, or a substituted or unsubstituted group as follows: aryl, heteroaryl, $C_1$-$C_8$ alkoxy, $C_1$-$C_8$ nitrate, $C_1$-$C_8$ alkyl, $C_1$-$C_8$ alkenyl, $C_1$-$C_8$ alkynyl,

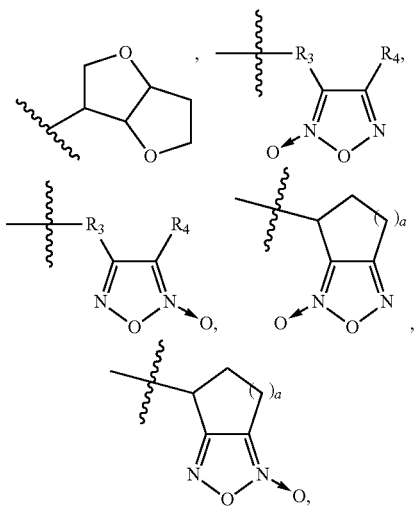

$(CH_2)_nO(CH_2)_mCH_3$, wherein $R_3$, $R_4$, a, m and n are independent from each other and have the same meanings as defined above;

$R_6$ and $R_7$ independently represent H, unsubstituted or substituted $C_1$-$C_8$ alkoxy or $C_1$-$C_8$ alkyl;

$R_8$ and $R_9$ independently represent H, unsubstituted or substituted $C_1$-$C_8$ alkoxy, $C_1$-$C_8$ nitrate or $C_1$-$C_8$ alkyl.

According to a preferred embodiment of the invention, the pharmaceutically acceptable excipients include one or more disintegrants and/or one or more fillers. Preferably, among the pharmaceutically acceptable excipients, at least one disintegrant has a particle size of 100 μm or less, and/or at least one filler has a particle size of 100 μm or less. More preferably, the above-mentioned at least one disintegrant and/or at least one filler have a particle size of 95 μm or less, such as 90 μm or less, 85 μm or less, 80 μm or less, or 75 μm or less; more preferably, the above-mentioned at least one disintegrant and/or at least one filler have a particle size of 10 μm or more, such as 15 μm or more, 20 μm or more, 25 μm or more, or 30 μm or more. Preferably, the at least one disintegrant and/or at least one filler are microcrystalline cellulose.

As an example, the excipients in the invention may have particle size selected from 30 μm, 32 μm, 40 μm, 50 μm, 60 μm, 70 μm or 75 m.

According to an embodiment of the invention, the pharmaceutically acceptable excipients include a first pharmaceutically acceptable excipient and optionally a second pharmaceutically acceptable excipient.

According to the invention, the first pharmaceutically acceptable excipient may be selected from at least one of fillers and disintegrants; preferably, at least one of the fillers and/or the disintegrants have a particle size of 100 μm or less, such as 95 μm or less, 90 μm or less, 85 μm or less, 80 μm or less, or 75 μm or less; more preferably, at least one of the fillers and/or the disintegrants have a particle size of 10 μm or more, such as 15 μm or more, 20 μm or more, 25 μm or more, or 30 μm or more; more preferably, at least one of the fillers and/or the disintegrants have a particle size of 20 to 85 μm, for example 30 to 75 μm;

According to the invention, the second pharmaceutically acceptable excipient may be at least one selected from the group including but not limited to, lubricants, wetting agents, auxiliary lipids, glidants, sweeteners, flavoring agents, solvents, cosolvents, suspending agents, isotonic agents, buffers, preservatives, antioxidants, colorants, and foaming agents.

According to an exemplary embodiment of the invention, the filler is at least one selected from the group consisting of starch, lactose, lactose monohydrate, cellulose-lactose, pregelatinized starch, sucrose, mannitol, sorbitol, calcium phosphate, dextrin, microcrystalline cellulose, calcium hydrogen phosphate and mannitol-starch complex; for example, the filler is at least one selected from the group consisting of microcrystalline cellulose and mannitol;

According to an exemplary embodiment of the invention, the disintegrant is at least one selected from the group consisting of croscarmellose sodium, calcium carboxymethyl cellulose, sodium carboxymethyl starch, methyl cellulose, low-substituted hydroxypropyl cellulose, crospovidone and chitosan; for example, the disintegrant is at least one selected from the group consisting of croscarmellose sodium and crospovidone;

According to an exemplary embodiment of the invention, the lubricant is at least one selected from the group consisting of magnesium stearate, colloidal silica, talc, sodium lauryl sulfate, calcium stearate, polyethylene glycol 4000, polyethylene glycol 6000, sodium stearyl fumarate, glyceryl monostearate and hydrogenated vegetable oil; for example, the lubricant is at least one selected from magnesium stearate and colloidal silica.

According to an embodiment of the invention, the pharmaceutically acceptable excipients include microcrystalline cellulose and other excipients, wherein the microcrystalline cellulose may have a particle size of 95 μm or less, such as 90 μm or less, 85 μm or less, 80 μm or less, or 75 μm or less; more preferably, the microcrystalline cellulose may have a particle size of 10 μm or more, such as 15 μm or more, 20 μm or more, 25 μm or more, or 30 μm or more; as an example, the microcrystalline cellulose may have a particle size of 30 μm, 32 μm, 40 μm, 50 μm, 60 μm, 70 μm or 75 m.

According to an embodiment of the invention, it should be understood that the particle sizes of other solid excipients in the pharmaceutical preparations are not specifically limited in the invention, unless the particle size of a particular excipient is limited. It should be understood that, in addition to solid excipients, the excipients that are suitable for use in the pharmaceutical preparations of the invention may also be liquid or gel-like. For example, the suitable excipients may include excipients that are commercially available in various sizes, such as granular or micronized excipients. The suitable examples include colloidal silica with the surface area of about 200 m$^2$/g.

According to an exemplary embodiment of the invention, the types of pharmaceutically acceptable salts of the neutral endopeptidase inhibitor and those of the compound of formula (I) are the same or different, and are independently from each other selected from Na, K or ammonium salts (e.g., addition salts with NH$_3$); the types of the pharmaceutically acceptable prodrugs of the neutral endopeptidase inhibitor and those of the compound of formula (I) are the same or different, and are independently from each other selected from the group including but not limited to methyl ester, ethyl ester, propyl ester, isopropyl ester, butyl ester, isobutyl ester, tert-butyl ester.

According to an exemplary embodiment of the invention, the compounds of formula (I) have the structures shown as follows:

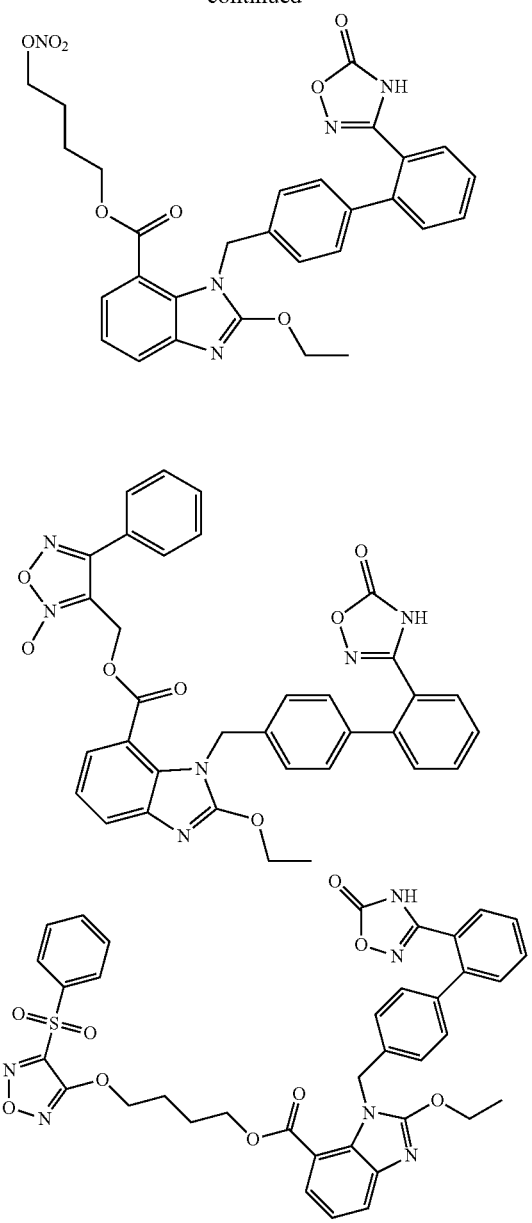

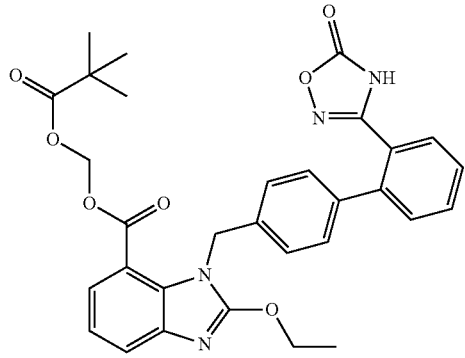

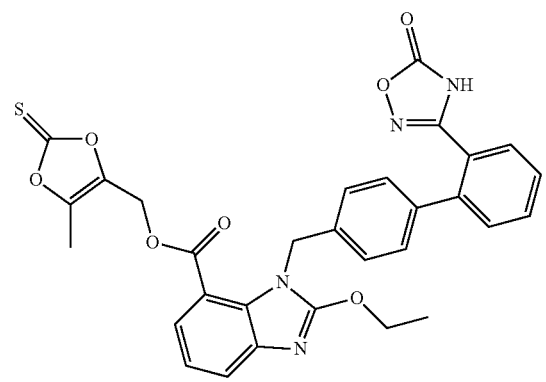

-continued
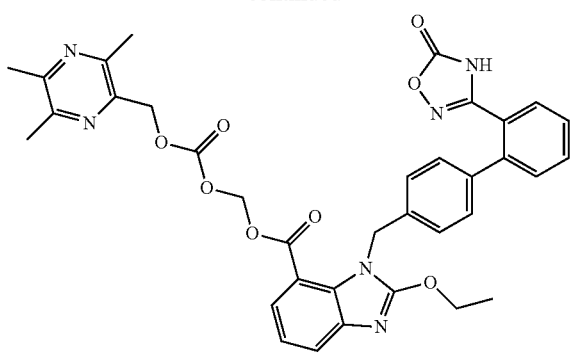
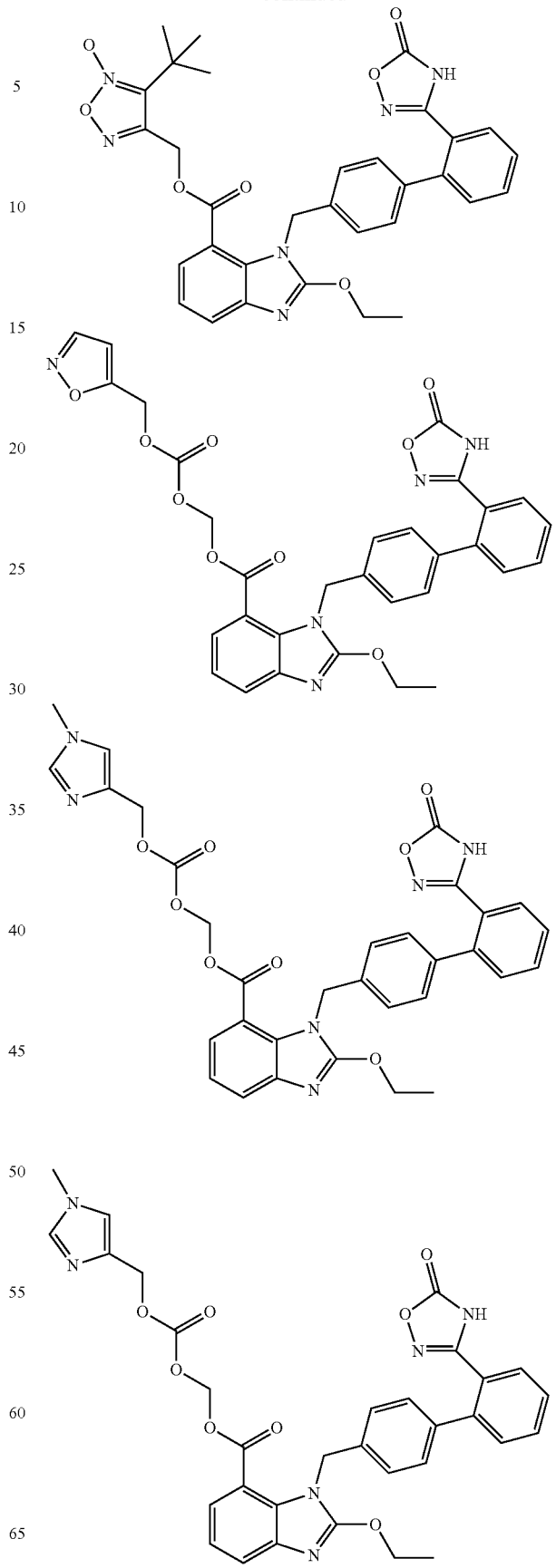

-continued

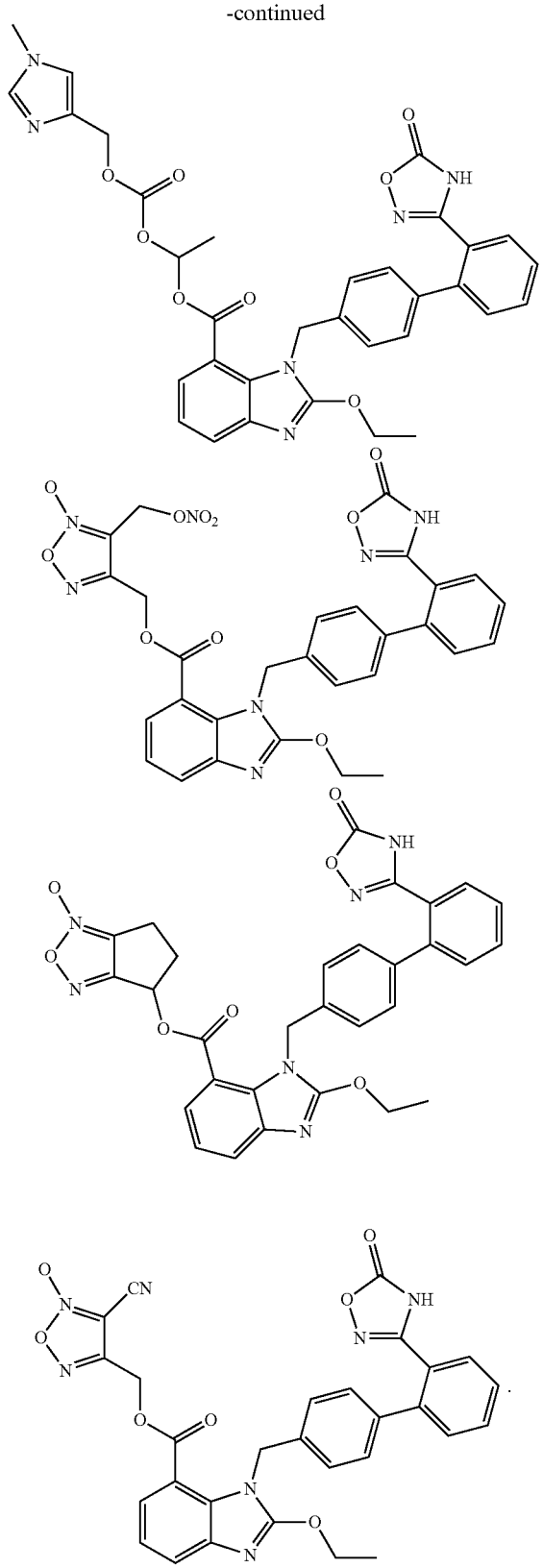

According to an exemplary embodiment of the invention, the first active component is at least one selected from the group consisting of the following compounds, the pharmacologically acceptable salt, prodrug or solvate thereof:

(S)-(2-biphenyl-4-yl)-1-(1H-tetrazol-5-yl)ethylamino)methylphosphonic acid,
(S)-5-(N-(2-(phosphonomethyl-amino)-3-(4-biphenyl)-propionyl)-2-aminoethyl)tetrazole,
(±)N-(1-oxo-2-mercaptomethyl-3-phenylpropionyl)glycine,
N-((2S)-2-(4-biphenylmethyl)-4-carboxy-5-phenoxy-valeryl)glycine,
N-(α-rhamnopyranosylphosphonamido)-L-leucine-L-tryptophan,
N—[N-((L)-1-carboxy-2-phenylethyl)-L-phenylalanyl]-(R)-alanine,
N—[N-[((1S)-carboxy-2-phenyl)ethyl]-(S)-phenylalanyl]-β-alanine,
N—(S)-[3-mercapto-2-(2-methylphenyl)propionyl]-(S)-2-methoxy-(R)-alanine,
3-[1,1'-biphenyl]-4-yl-N-[diphenoxyphosphinyl]methyl]-L-alanyl-β-alanine,
N-(1-(N-hydroxycarbamoyl-methyl)-1-cyclopentylcarbonyl)-L-phenylalanine,
N-[2-mercaptomethyl-3-phenyl-propionyl]-3-aminobenzoic acid,
4-[[2-(mercaptomethyl)-1-oxo-3-phenylpropyl]amino]benzoic acid,
N-[2-acetylsulfanylmethyl-3-phenyl-propionyl]-3-aminobenzoic acid,
N-[2-mercaptomethyl-3-(2-methylphenyl)-propionyl]-methionine,
N-(3-phenyl-2-(mercaptomethyl)-propionyl)-(S)-4-(methylsulfanyl)-methionine,
N-[1-(2-carboxy-4-phenylbutyl)-cyclopentylcarbonyl]-(S)-isoserine,
N-[2(S)-mercaptomethyl-3-(2-methylphenyl)propionyl]-(S)-isoserine,
N-(1-(3-(N-t-butoxycarbonyl-(S)-prolylamino)-2(S)-t-butoxy-carbonylpropyl)cyclopentylcarbonyl)-O-benzyl-(S)-serine,
3(S)-[2-(acetylsulfanylmethyl)-3-phenyl-propionyl]amino-ε-caprolactam,
N-[1-(acetylsulfanylmethyl)-cyclopentylcarbonyl]-(S)-methionine,
N-[2-acetylsulfanylmethyl-3-(2-methyl-phenyl)propionyl]-methionine,
N-[2(S)-mercaptomethyl-3-(2-methylphenyl)-propionyl]-methionine,
N-[2-(mercaptomethyl)-1-oxo-3-phenylpropyl]-β-alanine,
7-[[2-(mercaptomethyl)-1-oxo-3-phenylpropyl]amino]-heptanoic acid,
N—[N-[1(S)-carboxy-3-phenylpropyl]-(S)-phenylalanyl]-(S)-isoserine,
N-[1-[[1(S)-carbonyl-3-phenylpropyl]amino]-cyclopentylcarbonyl]-(S)-isoserine,
N-[1-[[1(S)-benzyloxycarbonyl-3-phenylpropyl]amino]-cyclopentylcarbonyl]-(S)-isoserine,
N—[N-[(L)-1-[(2,2-dimethyl-1,3-dioxolan-4-yl)-methoxy]carbonyl]-2-phenylethyl]-L-phenylalanyl]-(R)-alanine,
N-(2-carboxy-4-thienyl)-3-mercapto-2-benzylpropanamide,
2-(2-mercaptomethyl-3-phenylpropionamino)thiazol-4-yl-carboxylic acid,
(L)-(1-((2,2-dimethyl-1,3-dioxolan-4-yl)-methoxy)carbonyl)-2-phenylethyl)-L-phenylalanyl)-β-alanine,
cis-4-[[[1-[2-carboxy-3-(2-methoxyethoxy)propyl]-cyclopentyl]carbonyl]amino]-cyclohexanecarboxylic acid,
3-(1-[6-endo-hydroxymethylbicyclo[2,2,1]heptane-2-exo-carbamoyl]cyclopentyl)-2-(2-methoxyethyl)propanoic acid,
3-[1-(cis-4-carboxycarbonyl-cis-3-butylcyclohexyl-r-1-carbamoyl)cyclopentyl]-2S-(2-methoxy ethoxy-methyl)propanoic acid, (S)-cis-4-[1-[2-(5-indanyloxy-carbonyl)-3-(2-methoxy-ethoxy)propyl]-1-cyclopentylamido]-1-cyclohexanecarboxylic acid,
1,1'-[dithiobis-[2(S)-(2-methylbenzyl)-1-oxo-3,1-propylidene]]-bis-(S)-isoserine,
1,1'-[dithiobis-[2(S)-(2-methylbenzyl)-1-oxo-3,1-propylidene]]-bis-(S)-methionine,
4-(((2S,4R)-1-([1,1'-biphenyl]-4-yl)-5-ethoxy-4-methyl-5-oxopentan-2-yl)amino)-4-oxobutanoic acid,
N-(3-carboxy-1-oxopropyl)-(4S)-p-phenylphenylmethyl)-4-amino-2R-methylbutanoic acid.

In a preferred embodiment, the first active component is selected from at least one of the following compounds:
N-[1-(acetylsulfanylmethyl)cyclopentylcarbonyl]-(S)-methionine ethyl ester,
N-[2-acetylsulfanylmethyl-3-(2-methyl-phenyl)propionyl]-methionine ethyl ester,
N-(1-(3-(N-t-butoxycarbonyl-(S)-prolylamino)-2(S)-t-butoxy-carbonylpropyl)cyclopentylcarbonyl)-O-benzyl-(S)-serine methyl ester,
3(S)-[2-(acetylsulfanylmethyl)-3-phenyl-propionyl]amino-ε-caprolactam,
4-(((2S,4R)-1-([1,1'-biphenyl]-4-yl)-5-ethoxy-4-methyl-5-oxopentan-2-yl)amino)-4-oxobutanoic acid (AHU 377 or sacubitril),
N-(3-carboxy-1-oxopropyl)-(4S)-p-phenylphenylmethyl)-4-amino-2R-methylbutanoic acid,
Sodium N-(3-carboxy-1-oxopropyl)-(4S)-p-phenylphenylmethyl)-4-amino-2R-methylbutyrate,
Potassium N-(3-carboxy-1-oxopropyl)-(4S)-p-phenylphenylmethyl)-4-amino-2R-methylbutyrate,
Ethyl 4-(((2S,4R)-1-([1,1'-biphenyl]-4-yl)-5-ethoxy-4-methyl-5-oxopentan-2-yl)amino)-4-oxobutyrate (AHU 377 ethyl ester or sacubitril ethyl ester),
Sodium 4-(((2S,4R)-1-([1,1'-biphenyl]-4-yl)-5-ethoxy-4-methyl-5-oxopentan-2-yl)amino)-4-oxobutyrate (AHU 377 sodium salt or sacubitril sodium salt),
Potassium 4-(((2S,4R)-1-([1,1'-biphenyl]-4-yl)-5-ethoxy-4-methyl-5-oxopentan-2-yl)amino)-4-oxobutyrate (AHU 377 potassium salt or sacubitril potassium salt),
Ammonium 4-(((2S,4R)-1-([1,1'-biphenyl]-4-yl)-5-ethoxy-4-methyl-5-oxopentan-2-yl)amino)-4-oxobutyrate (AHU 377 ammonium salt or sacubitril ammonium salt).

In a preferred embodiment, the first active component is at least one selected from the group consisting of AHU 377, AHU 377 ethyl ester, AHU 377Na, AHU 377K, N-(3-carboxy-1-oxopropyl)-(4S)-p-phenylphenylmethyl)-4-amino-2R-methylbutanoic acid, sodium N-(3-carboxy-1-oxopropyl)-(4S)-p-phenylphenylmethyl)-4-amino-2R-methylbutyrate, potassium N-(3-carboxy-1-oxopropyl)-(4S)-p-phenylphenylmethyl)-4-amino-2R-methylbutyrate, or Ammonium 4-(((2S,4R)-1-([1,1'-biphenyl]-4-yl)-5-ethoxy-4-methyl-5-oxopentan-2-yl)amino)-4-oxobutyrate.

According to an exemplary embodiment of the invention, the second active component is selected from the potassium salts of the compounds of formula (I), such as the compounds of the following Formula (II):

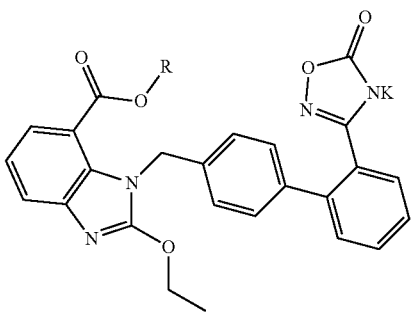

wherein, R is defined as above;

as an example, the potassium salts of the compounds of formula (I) are selected from the structures as shown below:

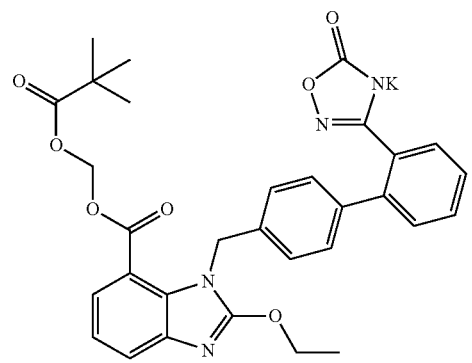

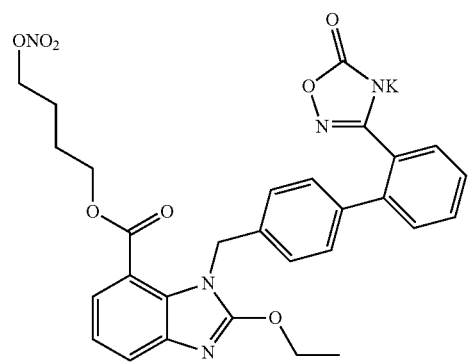

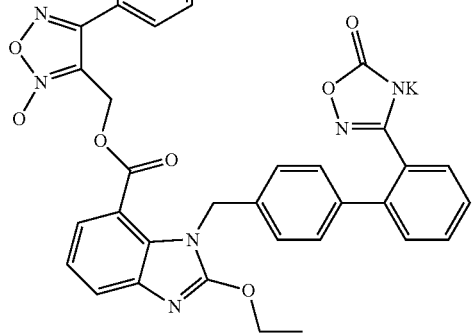

-continued
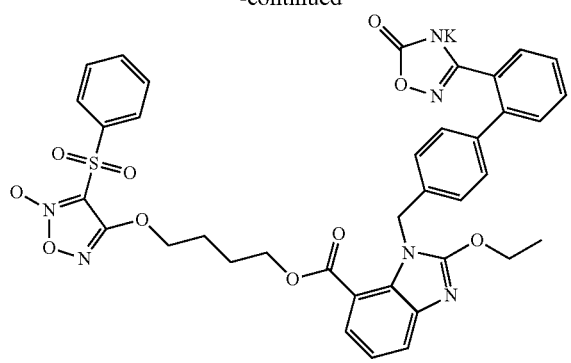
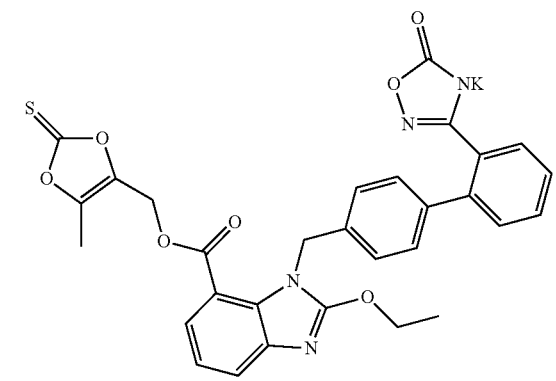
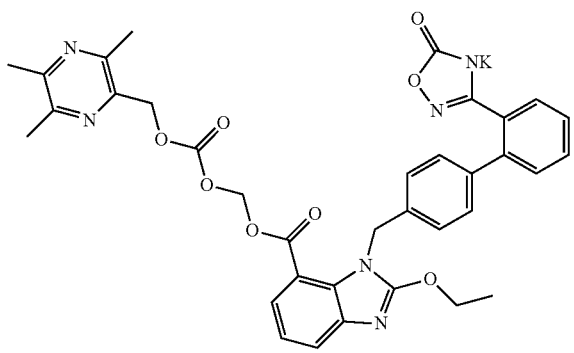
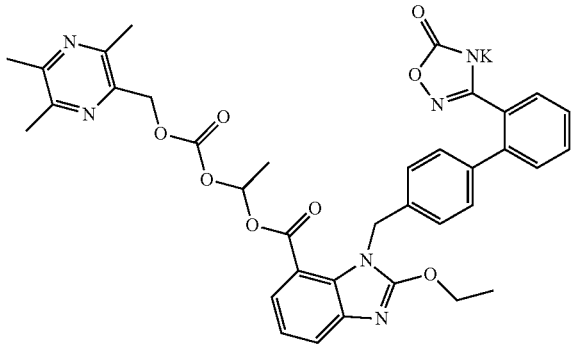
-continued
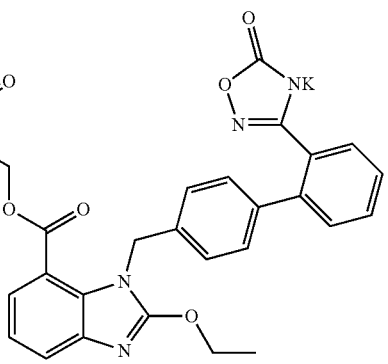
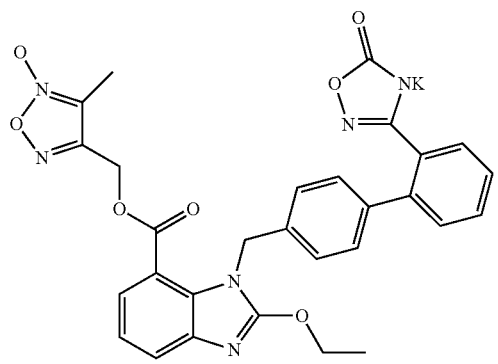
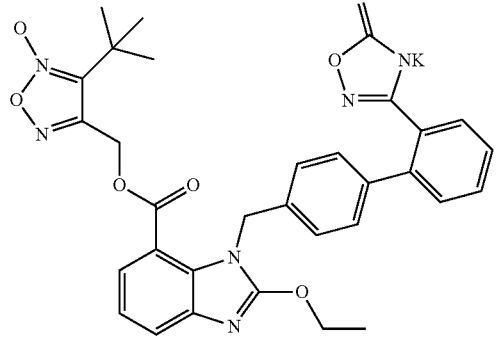
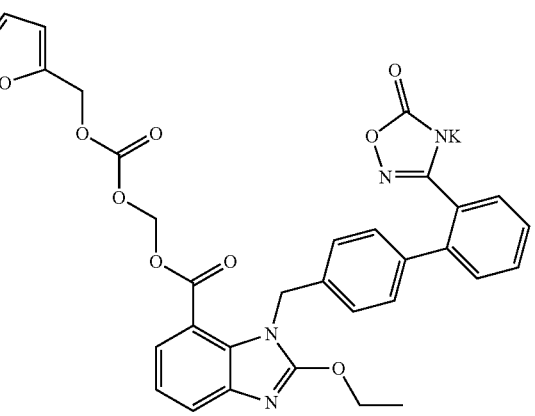

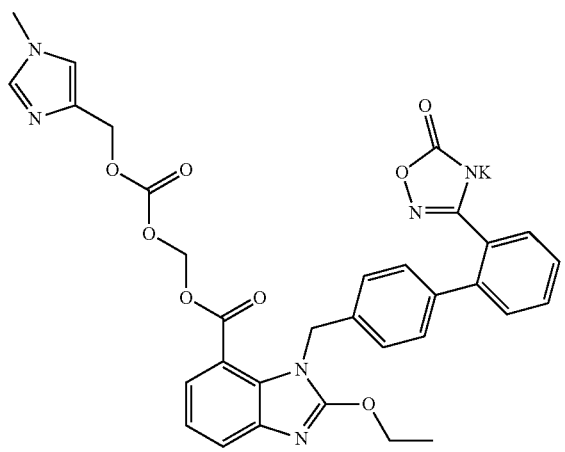

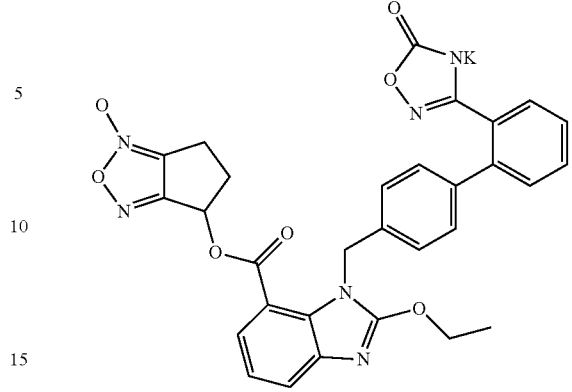

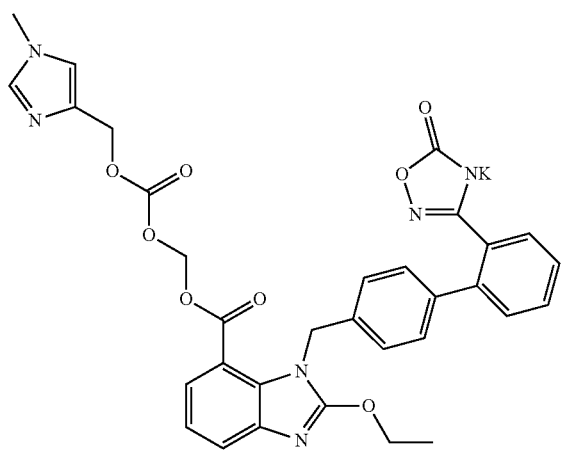

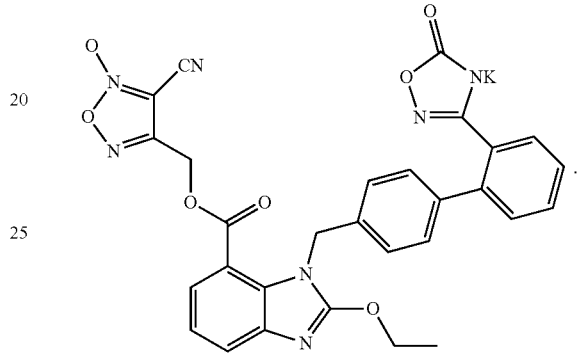

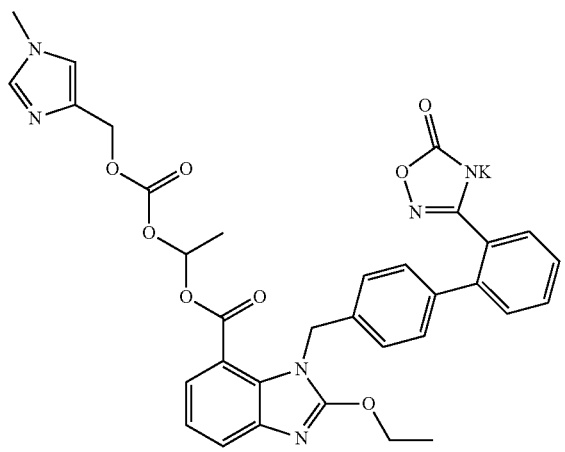

The pharmaceutical preparations of the invention may be formulated into various dosage forms suitable for oral, inhalation, rectal, topical, parenteral and other routes of administration, including but not limited to: the forms suitable for oral administration, such as powders, tablets (including various coated tablets, sustained-release or controlled-release tablets), lozenges, capsules (including soft and hard capsules), granules, pills, dispersible powders, aqueous or oily solutions, emulsions, elixirs, syrups, and the like; the forms suitable for inhalation administration, such as powders or liquid aerosols; the forms suitable for rectal administration, such as suppositories and the like; the forms suitable for topical administration, such as creams, ointments, gels, aqueous or oily solutions, and the like; the forms suitable for parenteral administration, especially by intravenous, subcutaneous or intramuscular injection, such as sterile aqueous or oily injections or lyophilized powders; preferably, the dosage forms may be tablets (including various coated tablets, sustained-release or controlled-release tablets), capsules (including soft capsules and hard capsules), and pills; according to an exemplary embodiment of the invention, the dosage forms may be tablets (including various coated tablets, sustained-release or controlled-release tablets). The invention also includes a form of drug pack, which is a combination of separate drugs and the separate drugs are administered in different dosage forms or at different administration intervals.

According to the pharmaceutical preparations of the invention, wherein the first active component and the second active component are at a weight ratio of (0.5-5):1, for example (0.5-3):1, such as at a weight ratio of 0.5:1, 1:1, 1.5:1, 1.8:1, 2:1, 2.5:1, 3:1, 3.5:1, 4:1, 4.5:1, 5:1.

In an embodiment of the invention, the pharmaceutical preparation includes:
5 to 70 parts by weight of the first active component,
5 to 70 parts by weight of the second active component,

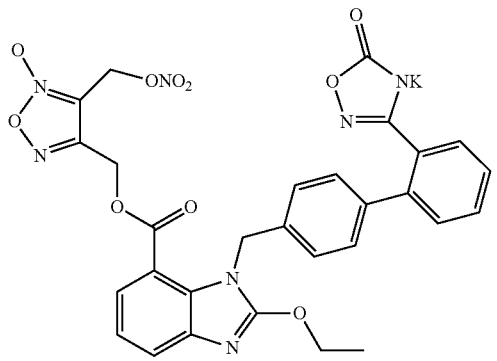

5 to 90 parts by weight of a filler,
2 to 35 parts by weight of a disintegrant,
0.1 to 10 parts by weight of a lubricant;
In an embodiment of the invention, the pharmaceutical preparation includes:
5 to 40 parts by weight of the first active component,
5 to 40 parts by weight of the second active component,
30 to 70 parts by weight of a filler,
8 to 20 parts by weight of a disintegrant,
0.5 to 5 parts by weight of a lubricant.
As an example, the pharmaceutical preparation includes:

| | |
|---|---|
| AHU377 ammonium or potassium salt | 5 to 70 parts by weight |
| potassium salt of compound 1 | 5 to 70 parts by weight |
| microcrystalline cellulose | 5 to 90 parts by weight |
| crospovidone | 2 to 35 parts by weight |
| magnesium stearate | 0.1 to 10 parts by weight; |

As an example, the pharmaceutical preparation includes:

| | |
|---|---|
| AHU377 ammonium salt | 5 to 40 parts by weight |
| potassium salt of compound 1 | 5 to 40 parts by weight |
| microcrystalline cellulose | 30 to 70 parts by weight |
| crospovidone | 8 to 20 parts by weight |
| magnesium stearate | 0.5 to 5 parts by weight; |

As an example, the pharmaceutical preparation includes:

| | |
|---|---|
| AHU377 ammonium salt | 5 to 40 parts by weight |
| potassium salt of compound 1 | 5 to 40 parts by weight |
| microcrystalline cellulose | 30 to 70 parts by weight |
| crospovidone | 8 to 20 parts by weight |
| magnesium stearate and colloidal silica | 0.5 to 5 parts by weight; |

The potassium salt of compound 1 is selected from the following compound:

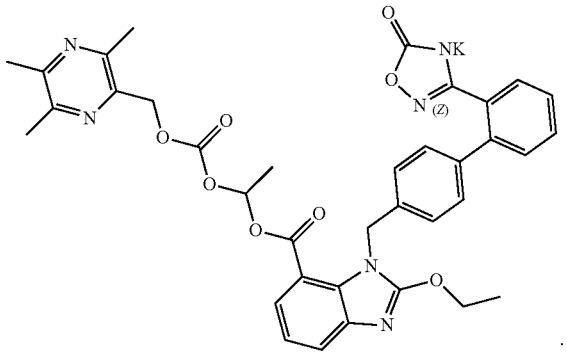

1K

The invention further provides a preparation method of the pharmaceutical preparations, comprising: mixing the first active component, the second active component and pharmaceutically acceptable excipients.

According to the invention, the preparation method may be: compressing the components and excipients into tablets or filling the components and excipients into capsules after dry granulation.

The invention also provides use of the pharmaceutical preparations in the manufacture of drugs for the prevention and/or treatment of cardiovascular diseases.

According to the invention, the cardiovascular diseases are selected from the group consisting of: hypertension, heart failure, chronic heart failure, coronary heart disease, rheumatic heart disease, congenital heart disease, left ventricular dysfunction, endothelial dysfunction, diastolic dysfunction, hypertrophic cardiomyopathy, diabetic cardiomyopathy, supraventricular and ventricular arrhythmias, atrial fibrillation, cardiac fibrosis, atrial flutter, detrimental vascular remodeling, myocardial infarction and sequelae thereof, atherosclerosis, angina, primary and secondary pulmonary hypertension, and renal vascular hypertension.

The invention also provides a method for the prevention and/or treatment of cardiovascular disease, comprising the administration of the pharmaceutical preparations to an individual in need.

Definition and Description of Terms

Unless defined otherwise, the definitions of groups and terms described in the specification and claims of the application, including the definitions as examples, exemplary definitions, preferred definitions, definitions listed in tables, definitions of specific compounds in the examples, etc., may be discretionarily combined with each other. It should be appreciated that the combined definitions of groups and the combined structures of compounds fall within the scope recited and claimed in the application.

When the numerical ranges described in the specification and claims of the application are defined as "integers", it should be understood that two endpoints of the ranges and each and every integer within the ranges are disclosed. For example, "integers from 0 to 10" should be understood that each of the integers 0, 1, 2, 3, 4, 5, 6, 7, 8, 9, and 10 is disclosed. When the numerical ranges are defined as "numbers", it should be understood that two endpoints of the ranges, each and every integer within the ranges and each decimal within the ranges are disclosed. For example, "numbers from 1 to 10" should be understood that not only each of the integers 0, 1, 2, 3, 4, 5, 6, 7, 8, 9 and 10, but also at least the sum of each integer and 0.1, 0.2, 0.3, 0.4, 0.5, 0.6, 0.7, 0.8, 0.9, respectively, is disclosed.

The term "one or more" in the specification of the application includes one or more than one, for example, including but not limited to 1, 2, 3, 4, 5, 6, 7, 8, 9 or 10.

The term "halogen" in the invention refers to fluorine, chlorine, bromine, or iodine.

The term "substitution/substitute(d)" refers to substitution with one or more arbitrary substituents. Suitable substituents include, but are not limited to, halogen, amino, cyano, nitro, carbonyl (oxo), mercapto (thio), hydroxyl, a ether group, carboxy, alkyl, alkoxy, alkenyl, alkynyl, alkenyloxy, alkynyloxy, aryl, heteroaryl, cycloalkyl, heterocyclic, substituted acyl, substituted sulfonyl, a substituted ester group, —CH=CHCO$_2$H, —CH=CHCO$_2$ alkyl. The substituents may be unsubstituted or optionally further substituted with one or more identical or different substituents selected from the above.

The term "alkyl", used alone or as a suffix or prefix, refers to a branched-chain and straight-chain saturated aliphatic hydrocarbon group having 1 to 20 carbon atoms (or if a specified number of carbon atoms provided, it refers to the specified number). For example, "$C_1$-$C_8$ alkyl" refers to a straight-chain and branched-chain alkyl group having 1, 2, 3, 4, 5, 6, 7 or 8 carbon atoms. Examples of alkyl include, but are not limited to, methyl, ethyl, n-propyl, isopropyl, n-butyl, isobutyl, sec-butyl, tert-butyl, pentyl, and hexyl. When an alkyl group is substituted with a substituent, it includes an alkyl group substituted with one or more halogens, e.g., an alkyl group substituted with one, two, three, four, five, six halogens, such as trifluoromethyl.

The term "alkenyl", used alone or as a suffix or prefix refers to a branched-chain and straight-chain aliphatic hydrocarbon group containing an alkenyl group or an olefin and having 2 to 20 carbon atoms (or if a specified number of carbon atoms provided, it refers to the specified number). For example, "$C_{2-6}$ alkenyl" refers to an alkenyl group having 2, 3, 4, 5 or 6 carbon atoms. Examples of alkenyl include, but are not limited to, vinyl, allyl, 1-propenyl, 1-butenyl, 2-butenyl, 3-butenyl, 2-methylbut-2-enyl, 3-methylbut-1-enyl, 1-pentenyl, 3-pentenyl and 4-hexenyl.

The term "alkynyl", used alone or as a suffix or prefix refers to a branched-chain and straight-chain aliphatic hydrocarbon group containing an alkynyl group or an alkyne and having 2 to 20 carbon atoms (or if a specified number of carbon atoms provided, it refers to the specified number); for example, ethynyl, propynyl (e.g., 1-propynyl, 2-propynyl), 3-butynyl, pentynyl, hexynyl, and 1-methylpent-2-ynyl.

The term "aryl" refers to an aromatic ring structure consisting of 5 to 20 carbon atoms. For example, an aromatic ring structure containing 5, 6, 7 and 8 carbon atoms may be a monocyclic aromatic group such as a phenyl; a ring structure containing 8, 9, 10, 11, 12, 13 or 14 carbon atoms may be polycyclic such as naphthyl. The aromatic ring may be substituted with the above-mentioned substituent(s) at one or more sites on the ring. The term "aryl" further includes a polycyclic ring system having two or more rings, wherein two adjacent rings share two or more carbons (called "fused rings"), and at least one of the rings is aryl and the other rings may be, for example, cycloalkyl, cycloalkenyl, cycloalkynyl, aryl and/or heterocyclic. Examples of polycycles include, but are not limited to, 2,3-dihydro-1,4-benzodioxohexadiene and 2,3-dihydro-1-benzofuran.

The term "cycloalkyl" refers to a saturated cyclic group having a specified number of carbon atoms. These terms may include fused or bridged polycyclic ring systems. The cycloalkyl group has 3 to 40 carbon atoms in its ring structure. In one embodiment, the cycloalkyl group has 3, 4, 5 or 6 carbon atoms in the ring. For example, "$C_{3-6}$ cycloalkyl" refers to a group such as cyclopropyl, cyclobutyl, cyclopentyl or cyclohexyl.

The term "heteroaryl" refers to a heteroaromatic heterocycle having at least one cyclic heteroatom (e.g., sulfur, oxygen or nitrogen). Heteroaryl groups include both monocyclic and polycyclic systems (e.g. having 2, 3 or 4 fused rings). Examples of heteroaryl include, but are not limited to, pyridyl, pyrimidinyl, pyrazinyl, pyridazinyl, triazinyl, furanyl, quinolinyl, isoquinolinyl, thienyl, imidazolyl, thiazolyl, indolyl, pyrrolyl, oxazolyl, benzofuranyl, benzothienyl, benzothiazolyl, isoxazolyl, pyrazolyl, triazolyl, tetrazolyl, indazoleyl, 1,2,4-thiadiazolyl, isothiazolyl, benzothienyl, purinyl, carbazolyl, benzimidazolyl, benzoxazolyl, azabenzoxazolyl, imidazothiazolyl, benzo[1,4]dioxinyl, benzo[1,3]dioxolyl, etc. The heteroaryl group has 3 to 40 carbon atoms in some embodiments, and 3 to 20 carbon atoms in other embodiments. In some embodiments, the heteroaryl group contains 3 to 14, 4 to 14, 3 to 7, or 5 to 6 ring-forming atoms. In some embodiments, the heteroaryl group has 1 to 4, 1 to 3 or 1 to 2 heteroatoms. In some embodiments, the heteroaryl group has 1 heteroatom.

Unless otherwise specified, the term "heterocyclic group" used herein refers to a saturated, unsaturated or partially saturated, mono-, bi- or tri-cyclic ring containing 3 to 20 atoms, among which 1, 2, 3, 4 or 5 atoms are selected from nitrogen, sulfur or oxygen, and unless otherwise specified, are attached via carbon or nitrogen atoms, wherein the —CH$_2$— group is optionally replaced by —C(O)—; and unless otherwise specified to the contrary, a ring nitrogen or ring sulfur atom is optionally oxidized to form N-oxide or S-oxide, or a ring nitrogen atom is optionally quaternized; wherein —NH in the ring is optionally substituted with acetyl, formyl, methyl or methylsulfonyl; and wherein the ring is optionally substituted with one or more halogens. It should be understood that when the total number of S and O atoms in the heterocyclic group exceeds 1, these heteroatoms are not adjacent to each other. If the heterocyclic group is bicyclic or tricyclic, at least one ring may optionally be a heteroaromatic ring or an aromatic ring, with the proviso that the at least one ring is non-heteroaromatic. If the heterocyclic group is monocyclic, it is not necessarily an aromatic group. Examples of heterocyclic groups include, but are not limited to, piperidinyl, N-acetylpiperidinyl, N-methylpiperidinyl, N-formylpiperazinyl, N-methylsulfonylpiperazinyl, homopiperazinyl, piperazinyl, azetidinyl, oxetidinyl, morpholinyl, tetrahydroisoquinolinyl, tetrahydroquinolinyl, dihydroindolyl, tetrahydropyranyl, dihydro-2H-pyranyl, tetrahydrofuranyl, tetrahydrothiopyranyl, tetrahydrothiopyran-1-oxide, tetrahydrothiopyran-1,1-dioxide, 1H-pyridin-2-one, and 2,5-dioxoimidazolidinyl.

The compounds of the invention may also contain one or more asymmetric centers, depending on the position and the nature of different substituents. Asymmetric carbon atoms can exist in either the (R) or (S) configuration. When there is only one asymmetric center, a racemic mixture is produced, and when there are multiple asymmetric centers, a mixture of diastereomers is obtained. In some cases, there may also be asymmetries due to hindered rotation around particular bonds, for example, the central bond connecting two substituted aromatic rings of a particular compound. Moreover, the substituents may also be in the cis- or trans-configuration.

Each compound of formula (I) also includes all the possible stereoisomers thereof, which are single stereoisomer or any mixture of the stereoisomers (e.g., R-isomer or S-isomer, or E-isomer or Z-isomer) in any proportion. Single stereoisomer of the compounds of the invention (e.g., single enantiomer or single diastereomer) may be separated by any suitable method in prior art (such as chromatography, especially, e.g., chiral chromatography).

Furthermore, the compounds may also exist in the tautomeric forms. The compounds of the invention include all the possible tautomers of the compounds of formula (I), which is single tautomer or any mixture of the tautomers in any proportion.

These isomers and their mixtures are all to be included in the scope of this invention.

It will be understood by those skilled in the art that the neutral endopeptidase inhibitor and the compounds of formula (I) of the invention may be present in the form of various pharmaceutically acceptable salts. These compounds may form acid addition salts if they have alkaline centers, and may form alkali addition salts if they have acidic centers, and may form internal salts if they have both acidic centers (e.g., carboxyl groups) and alkaline centers (e.g., amino groups).

In the invention, the acid addition salts include, but are not limited to, hydrochlorid, hydrofluorid, hydrobromid, hydroiodid, sulfate, pyrosulfate, phosphate, nitrate, methanesulfonate, ethanesulfonate, 2-hydroxyethanesulfonate, benzenesulfonate, toluenesulfonate, sulfamate, 2-naphthalenesulfonate, formate, acetoacetic acid, pyruvic acid, laurate, cinnamate, benzoate, acetate, dihydroxyacetate, trifluoroacetate, trimethylacetate, propionate, butyrate, caproate, caprylate, undecanoate, stearate, ascorbate, camphorate, camphorsulfonate, citrate, fumarate, malate, maleate, hydroxymaleate, oxalate, salicylate, succinate, gluconate, quinate, dihydroxynaphthoate, glycolate, tartarate, lactate, 2-(4-hydroxybenzoyl) benzoate, cyclopentylpropionate, digluconate, 3-hydroxy-2-naphthoate, nicotinate, pamoate, pectate, 3-phenylpropionate, picrate, pivalate, itaconate, trifluoromethanesulfonate, dodecyl sulfate, p-toluenesulfonate, naphthalenedisulfonate, malonate, adipate, alginate, mandelate, glucoheptonate, glycerophosphorate, sulfosalicylate, hemi-sulfate or thiocyanate, aspartate, etc; the base addition salts such as alkali metal salts, alkali earth metal salts and ammonium salts, etc., specifically including, but not limited to, sodium salts, lithium salts, potassium salts, ammonium salts, aluminum salts, magnesium salts, calcium salts, barium salts, iron salts, ferrous salts, manganese salts, manganous salts, zinc salts, ammonium salts (including salts formed with $NH_3$ and organic amine ($NH_4$ salts), methylammonium salts, trimethylammonium salts, diethylammonium salts, triethylammonium salts, propylammonium salts, tripropylammonium salts, isopropylammonium salts, tert-butylammonium salts, N,N'-dibenzylethylenediammonium salts, dicyclohexylammonium salts, 1,6-hexanediammonium salts, benzylammonium salts, ethanolammonium salts, N,N-dimethylethanolammonium salts, N, N-diethylethanolammonium salts, triethanolammonium salts, tromethamine salts, lysine salts, arginine salts, histidine salts, glucosammonium salts, N-methylglucosammonium salts, dimethylglucosammonium salts, ethylglucosammonium salts, meglumine salts, betaine salts, caffeine salts, chloroprocaine salts, procaine salts, lidocaine salts, pyridine salts, methylpyridine salts, piperidine salts, morpholine salts, piperazine salts, purine salts, cocaine salts, choline salts, etc.

Beneficial effects of the invention include:

1. The pharmaceutical preparations of the invention effectively improve the viscosity (which causes the problem that the preparations cannot be disintegrated) of the active ingredients when encountering water, and thus promote the disintegration of the pharmaceutical preparations so as to release drugs.

2. The pharmaceutical preparations of the invention utilize conventional pharmaceutical excipients, neither require the addition of special excipients nor require preparing into special dosage forms. The pharmaceutical preparations of the invention achieve fast disintegration by adjusting the formulations so as to dissolve the active ingredients and improve the bioavailability.

3. The inventors unexpectedly found that good flowability and high uniform granulation of the preparation materials are achieved by controlling the particle sizes of the key excipients. The control of the particle sizes of the key excipients ensures the effective disintegration of the active substances (active ingredients) having strong hygroscopicity and becoming sticky after absorbing moisture, facilates the dissolution of the active ingredients and improves the bioavailability.

4. The pharmaceutical preparations of the invention may be used for preventing and/or treating cardiovascular diseases such as hypertension and chronic heart failure.

5. The pharmaceutical preparations of the invention can be administered by routes such as oral administration, which is convenient to use.

6. The pharmaceutical preparations of the invention can improve the drug-forming properties of the active ingredients and increase the compliance of patients.

EXAMPLES

The technical solutions of the invention will be further illustrated in detail in combination with specific examples. The following examples are intended to give an exemplary description and illustration of the invention, rather than set any limitation on the scope of protection of the invention. All technologies implemented based on the above-mentioned content of the invention fall within the scope of protection of the invention.

Unless other specified, the raw materials and reagents in the following examples are all either commercially available products, or can be prepared by methods known in the art.

The first active component: it was prepared according to the method in Example 1.

The second active component: the compounds of formula (I) could be prepared by methods known in the art, for example, the preparation method as disclosed in CN103709154A, which is hereby incorporated by reference in its entirety. The compounds of formula (II) could be prepared by contacting the compounds of formula (I) with potassium salt reagents. Preferably, the compounds of formula (II) were prepared by contacting the potassium salt reagents in solvents with the compounds of formula (I) (see the preparation process in Example 2 for details).

General preparation method of the pharmaceutical preparations of the invention

The first active component and the second active component were weighed according to the formulation amounts, and microcrystalline cellulose, mannitol, and colloidal silica were added. After passing through 40 mesh sieve, crospovidone at the formulation amount was added and then mixed for 5 to 10 min. After being mixed homogenously, magnesium stearate at the formulation amount was weighted in, and mixed well. Then, the mixture was subjected to dry granulation to give granules.

The excipients and the amounts thereof were adjusted according to the formulation of the specific example.

Example 1: Preparation of AHU 377 Ammonium Salt

Preparation of Ammonium 4-(((2S,4R)-1-([1,1'-biphenyl]-4-yl)-5-ethoxy-4-methyl-5-oxopentan-2-yl)amino)-4-oxobutyrate (AHU 377 Ammonium Salt or Sacubitril Ammonium Salt)

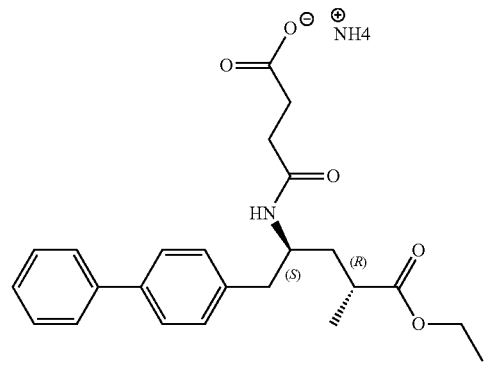

Sacubitril was added to acetone solvent, stirred at room temperature, and cooled to 0 to 10° C. A slight excess of concentrated aqueous ammonia was added dropwise, and after the addition, the mixture was stirred for 4 h, filtered, washed with acetone, and dried under vacuum to give the target compound with a purity greater than 99.5%, MS: m/z=412.3 (M+H)$^+$.

The AHU 377K was prepared in a similar way, except for replacing concentrated aqueous ammonia with potassium hydroxide.

Example 2: Preparation of Potassium Salt of Compound 1

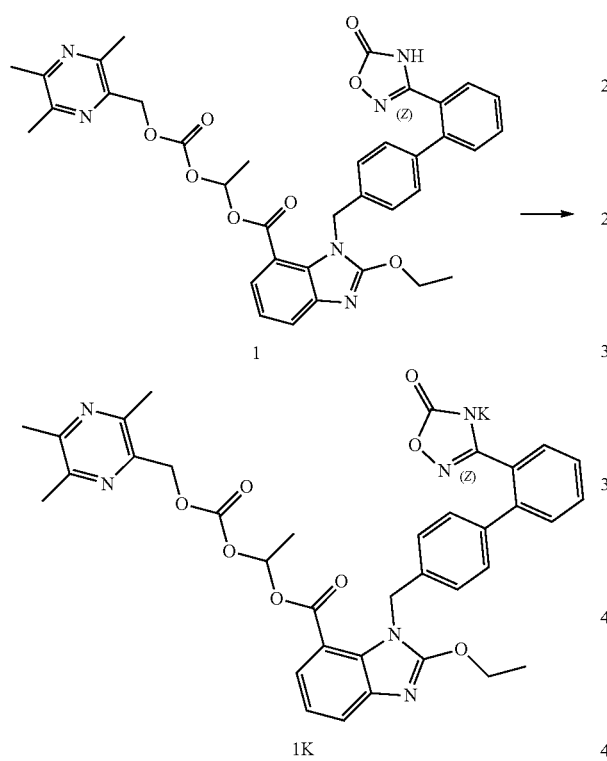

Compound 1 (1.0 g) was dissolved in dichloromethane (5 ml), and stirred at room temperature to form a solution. Potassium phthalimide (0.27 g) was added to the solution, and the reaction mixture was maintained at a constant temperature for 4 h, cooled to −50° C., and filtered. The solvent was removed by rotary evaporation to give a solid, namely, potassium salt of compound 1 (amorphous).

Melting point: 135-145° C.

MS/HRMS m/z: 717 [M+H]$^+$; 677 [M-K].

$^1$H-NMR (400 MHz, DMSO-d$_6$) δ:1.44 (t, 3H), 1.46 (t, 3H), 2.38 (s, 3H), 2.41 (s, 3H), 2.44 (s, 3H), 4.64 (q, 2H), 5.29 (d, 1H), 5.32 (d, 1H), 5.52 (d, 1H), 5.56 (d, 1H), 6.86 (q, 1H), 6.90 (d, 2H), 7.18 (m, 2H), 7.22 (d, 2H), 7.33 (m, 1H), 7.36 (m, 1H), 7.46 (d, 1H), 7.52 (dd, 1H), 7.75 (d, 1H).

It was found that the composition consisting of the API products of Examples 1 and 2 (100 mg:50 mg) (without excipients for the pharmaceutical preparation) had a moisture-absorption weight gain of 28.31% over 5 days, at a relative humidity of 92.5% and a temperature of 25° C.

Example 3

| Ingredient | Amount |
|---|---|
| AHU 377K | 100 mg |
| potassium salt of compound 1 | 30 mg |
| microcrystalline cellulose (average particle size: 30 μm) | 300 mg |
| crospovidone | 50 mg |
| magnesium stearate | 3 mg |
| colloidal silica | 8 mg |

Example 4

| Ingredient | Amount |
|---|---|
| AHU377 ammonium salt | 100 mg |
| potassium salt of compound 1 | 50 mg |
| microcrystalline cellulose (average particle size: 32 μm) | 300 mg |
| crospovidone | 50 mg |
| magnesium stearate | 3 mg |
| colloidal silica | 8 mg |

Example 5

| Ingredient | Amount |
|---|---|
| AHU377 ammonium salt | 90 mg |
| potassium salt of compound 1 | 30 mg |
| microcrystalline cellulose (average particle size: 50 μm) | 300 mg |
| croscarmellose sodium | 50 mg |
| magnesium stearate | 3 mg |
| colloidal silica | 8 mg |

Example 6

| Ingredient | Amount |
|---|---|
| AHU377 ammonium salt | 100 mg |
| potassium salt of compound 1 | 50 mg |
| microcrystalline cellulose (average particle size: 75 μm) | 300 mg |
| crospovidone | 50 mg |
| magnesium stearate | 3 mg |
| colloidal silica | 8 mg |

Example 7

| Ingredient | Amount |
|---|---|
| AHU377 ammonium salt | 100 mg |
| potassium salt of compound 1 | 50 mg |
| lactose | 100 mg |
| microcrystalline cellulose (average particle size: 85 μm) | 200 mg |

-continued

| Ingredient | Amount |
| --- | --- |
| crospovidone | 50 mg |
| magnesium stearate | 3 mg |
| colloidal silica | 8 mg |

Example 8

| Ingredient | Amount |
| --- | --- |
| AHU377 ammonium salt | 100 mg |
| potassium salt of compound 1 | 50 mg |
| microcrystalline cellulose (average particle size: 20 μm) | 300 mg |
| croscarmellose sodium | 50 mg |
| magnesium stearate | 10 mg |

Example 9

| Ingredient | Amount |
| --- | --- |
| AHU377 ammonium salt | 100 mg |
| potassium salt of compound 1 | 50 mg |
| mannitol | 100 mg |
| microcrystalline cellulose (average particle size: 32 μm) | 200 mg |
| croscarmellose sodium | 50 mg |
| magnesium stearate | 3 mg |
| colloidal silica | 8 mg |

Example 10

| Ingredient | Amount |
| --- | --- |
| AHU377 ammonium salt | 90 mg |
| potassium salt of compound 1 | 30 mg |
| lactose | 100 mg |
| microcrystalline cellulose (average particle size: 32 μm) | 200 mg |
| crospovidone | 50 mg |
| talc | 3 mg |
| colloidal silica | 8 mg |

Example 11

| Ingredient | Amount |
| --- | --- |
| AHU377 ammonium salt | 100 mg |
| potassium salt of compound 1 | 50 mg |
| lactose | 100 mg |
| microcrystalline cellulose (average particle size: 32 μm) | 200 mg |
| crospovidone | 50 mg |
| sodium stearyl fumarate | 3 mg |
| colloidal silica | 8 mg |

In the preparation process of Example 3-11, the materials had good flowability, and the mixture gave uniform granules. After testing, the differences in tablet weights of the products obtained in Examples 3-11 were within ±5%, and tablet hardness was between 80-120N.

It should be understood by those skilled in the art that the examples of the invention are not limited to Examples 3-11 as listed, but also include the replacement with other excipients as listed in the specification, e.g., replacing lactose or mannitol with cellulose lactose, pregelatinized starch, sucrose, sorbitol, calcium phosphate, etc.; replacing croscarmellose sodium or crospovidone with calcium carboxymethyl cellulose, sodium carboxymethyl starch, methyl cellulose, low-substituted hydroxypropyl cellulose, chitosan, etc.; replacing magnesium stearate, sodium stearyl fumarate or colloidal silica with talc, sodium lauryl sulfate, calcium stearate, polyethylene glycol 4000, polyethylene glycol 6000, glyceryl monostearate, hydrogenated vegetable oil, etc. After testing, it was found that the dissolution of the pharmaceutical preparations obtained after the replacement of excipients was close to that of Examples 3-11.

Comparative Example 1

| Ingredient | Amount |
| --- | --- |
| AHU377 ammonium salt | 100 mg |
| potassium salt of compound 1 | 50 mg |
| mannitol | 100 mg |
| microcrystalline cellulose (average particle size: 120 μm) | 200 mg |
| crospovidone | 50 mg |
| magnesium stearate | 3 mg |
| colloidal silica | 8 mg |

Comparative Example 2

| Ingredient | Amount |
| --- | --- |
| AHU377 ammonium salt | 90 mg |
| potassium salt of compound 1 | 30 mg |
| mannitol | 100 mg |
| microcrystalline cellulose (average particle size: 120 μm) | 200 mg |
| crospovidone | 50 mg |
| magnesium stearate | 3 mg |
| colloidal silica | 8 mg |

Example 12

Pharmaceutical preparations were obtained according to the formulations of Examples 3-11 and Comparative Examples 1-2 by the general method and they were subjected to the determination of drug dissolution.

Instrument: RC-12AD Intelligent Dissolution Tester (from Tianda Tianfa Technology Co., Ltd., Tianjin)

Method: Paddle method, 5 ml of sample was filtered and 2 ml of initial filtrate was discarded. The subsequent filtrate was placed in a vial for liquid-phase. The filter was polyethersulfone membranes 3 with 0.45 μm pore diameter.

Medium: 900 ml of 0.1 M HCl containing 0.5% Tween 80

Rotate speed: 50 rpm

Temperature: 37° C.

The dissolution data of the obtained products were shown in the table below:

| Serial number | Dissolution rate | 5 min | 10 min | 15 min | 30 min | 45 min | 60 min |
| --- | --- | --- | --- | --- | --- | --- | --- |
| Example 3 | accumulated dissolution of the first active component % | 38.12 | 71.94 | 78.45 | 88.21 | 93.74 | 96.13 |
| | accumulated dissolution of the second active component % | 28.21 | 50.45 | 58.16 | 73.94 | 85.16 | 91.46 |
| Example 4 | accumulated dissolution of the first active component % | 40.21 | 72.36 | 85.42 | 90.12 | 94.36 | 97.31 |
| | accumulated dissolution of the second active component % | 35.24 | 52.65 | 61.23 | 76.78 | 85.94 | 94.36 |
| Example 5 | accumulated dissolution of the first active component % | 33.02 | 60.49 | 70.41 | 82.62 | 87.77 | 92.65 |
| | accumulated dissolution of the second active component % | 23.31 | 44.45 | 50.17 | 67.32 | 80.16 | 89.18 |
| Example 6 | accumulated dissolution of the first active component % | 21.35 | 42.92 | 55.76 | 64.96 | 75.45 | 80.11 |
| | accumulated dissolution of the second active component % | 18.68 | 30.26 | 42.62 | 55.33 | 60.19 | 76.30 |
| Example 7 | accumulated dissolution of the first active component % | 25.32 | 47.46 | 58.71 | 62.53 | 68.61 | 75.82 |
| | accumulated dissolution of the second active component % | 15.21 | 31.44 | 42.36 | 49.95 | 57.16 | 66.73 |
| Example 8 | accumulated dissolution of the first active component % | 34.21 | 59.41 | 68.62 | 79.78 | 85.34 | 92.25 |
| | accumulated dissolution of the second active component % | 22.12 | 45.31 | 48.61 | 65.23 | 77.79 | 88.12 |
| Example 9 | accumulated dissolution of the first active component % | 27.46 | 55.89 | 70.43 | 77.47 | 86.12 | 90.53 |
| | accumulated dissolution of the second active component % | 18.26 | 36.63 | 50.16 | 62.09 | 76.76 | 86.08 |
| Example 10 | accumulated dissolution of the first active component % | 12.35 | 23.36 | 48.18 | 66.27 | 80.13 | 90.62 |
| | accumulated dissolution of the second active component % | 10.35 | 22.54 | 33.95 | 52.31 | 75.56 | 82.31 |
| Example 11 | accumulated dissolution of the first active component % | 13.35 | 25.63 | 47.46 | 69.92 | 82.37 | 92.16 |
| | accumulated dissolution of the second active component % | 9.43 | 20.08 | 35.64 | 55.23 | 76.71 | 84.29 |
| Comparative Example 1 | accumulated dissolution of the first active component % | 6.32 | 15.61 | 29.43 | 35.12 | 45.35 | 51.26 |
| | accumulated dissolution of the second active component % | 5.23 | 17.67 | 28.46 | 32.74 | 1.41 | 47.63 |
| Comparative Example 2 | accumulated dissolution of the first active component % | 1.69 | 3.87 | 7.16 | 23.25 | 30.09 | 45.52 |
| | accumulated dissolution of the second active component % | 4.21 | 10.47 | 20.06 | 25.82 | 33.13 | 40.64 |

It was found that the pharmaceutical preparations obtained in this application had good dissolution property. However, when microcrystalline cellulose with an unsuitable particle size was used, it had a greater influence on the dissolution of the products.

The embodiments of the invention were described above. However, the invention is not limited to the above embodiments. Any modification, equivalent replacement, improvement, etc., falling within the spirit and scope of protection of the invention, are intended to be included within the scope of protection of the invention.

The invention claimed is:

1. A pharmaceutical preparation comprising a first active component, a second active component and a pharmaceutically acceptable excipient, wherein said first active component is 4-(((2S,4R)-1-([1,1'-biphenyl]-4-yl)-5-ethoxy-4-methyl-5-oxopentan-2-yl)amino)-4-oxobutanoic acid or a pharmaceutically acceptable salt thereof;

said second active component is selected from the following compounds:

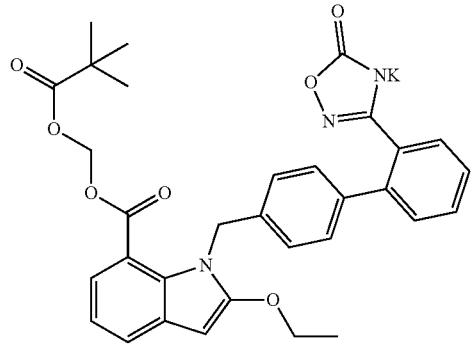

,

-continued

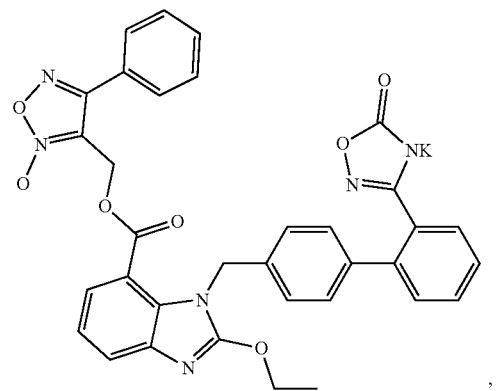

,

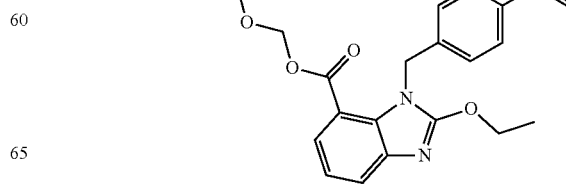

,

31
-continued
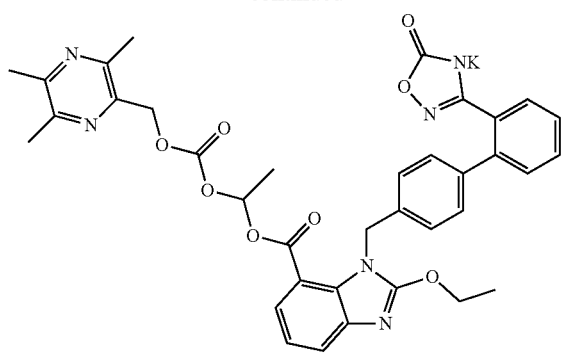
,
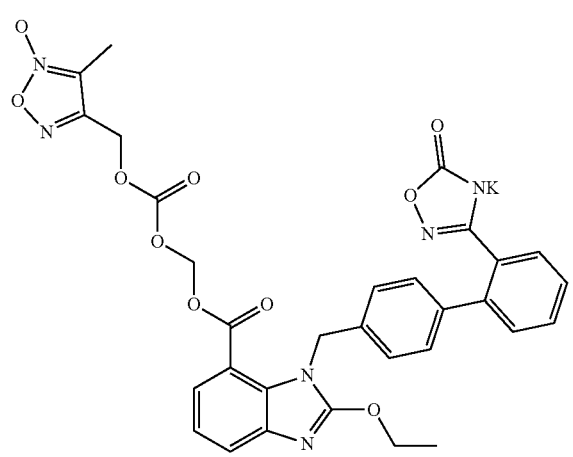
,
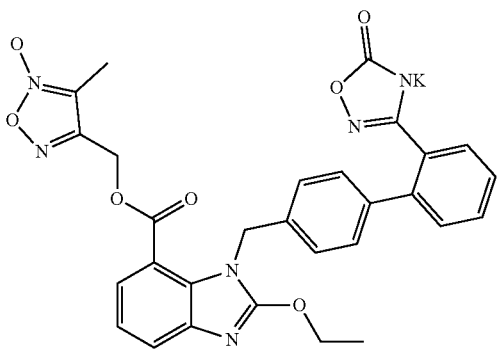
,
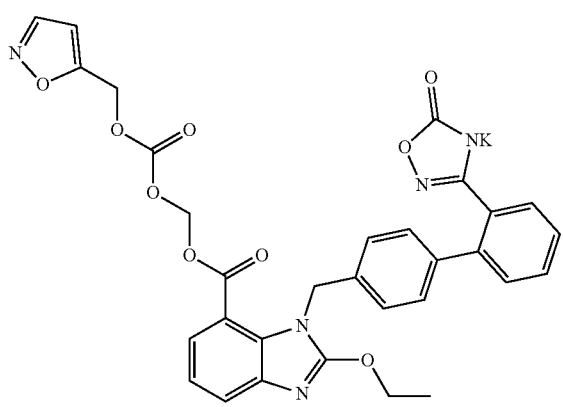
,
32
-continued
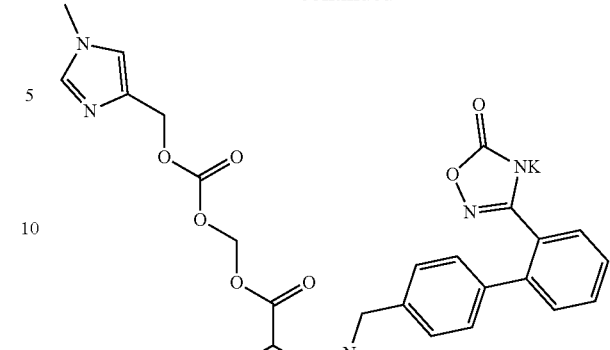
,
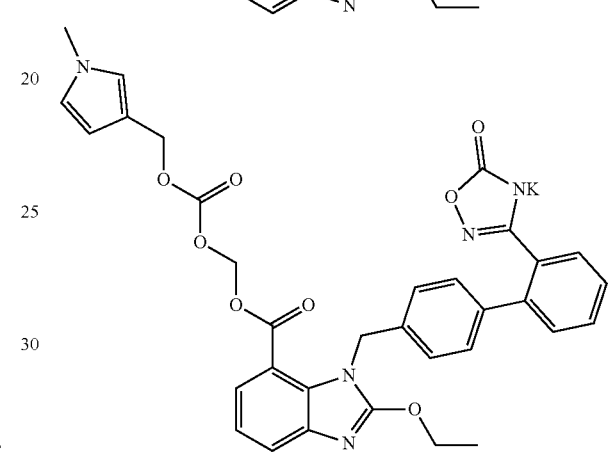
,
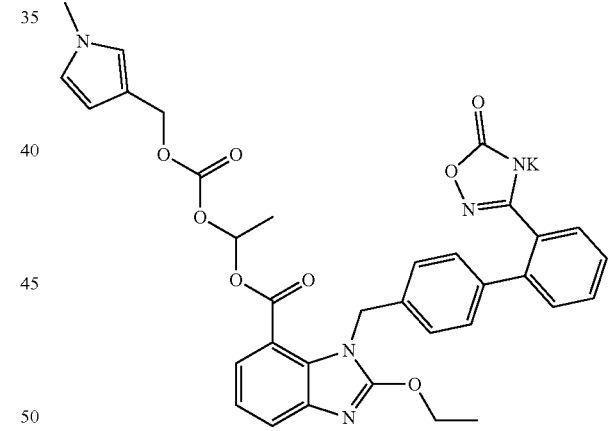
,
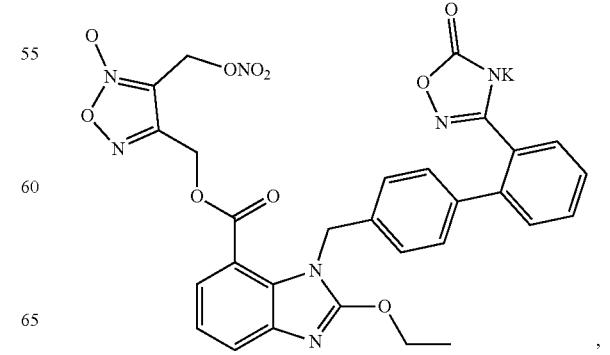
, -continued

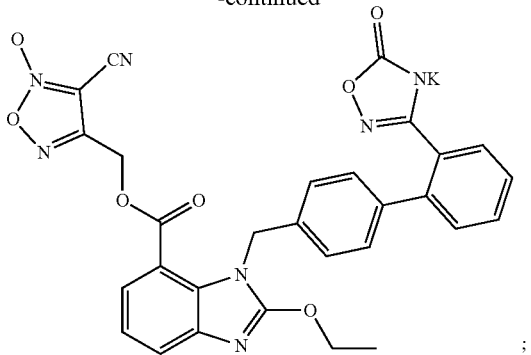

and
said pharmaceutically acceptable excipients include microcrystalline cellulose and another excipient, wherein said microcrystalline cellulose has a particle size of 95 μm or less.

2. A method for treating a cardiovascular disease, comprising administering the pharmaceutical preparation of claim 1 to a subject in need thereof, wherein said cardiovascular diseases is selected from hypertension, heart failure, chronic heart failure, coronary heart disease, rheumatic heart disease, congenital heart disease, left ventricular dysfunction, endothelial dysfunction, diastolic dysfunction, hypertrophic cardiomyopathy, diabetic cardiomyopathy, supraventricular and ventricular arrhythmias, atrial fibrillation, cardiac fibrosis, atrial flutter, detrimental vascular remodeling, myocardial infarction and sequelae thereof, atherosclerosis, angina, primary and secondary pulmonary hypertension, and renal vascular hypertension.

3. The pharmaceutical preparation of claim 1, wherein said second active component is selected from the following compound:

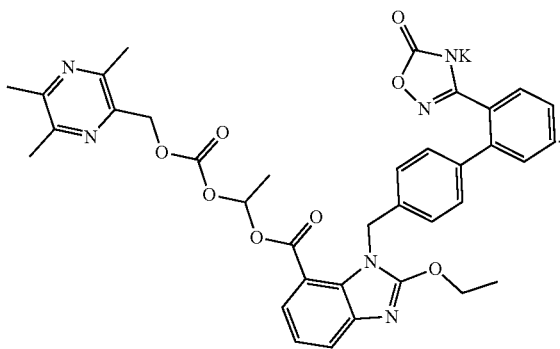

4. The pharmaceutical preparation of claim 1, wherein said microcrystalline cellulose has a particle size of from 10 μm to 90 μm.

5. The pharmaceutical preparation of claim 1, wherein said microcrystalline cellulose has a particle size of from 15 μm to 85 μm.

6. The pharmaceutical preparation of claim 1, wherein said microcrystalline cellulose has a particle size of from 20 μm to 85 μm.

7. The pharmaceutical preparation of claim 1, wherein said microcrystalline cellulose has a particle size of from 20 μm to 75 μm.

8. The pharmaceutical preparation of claim 1, wherein said pharmaceutically acceptable excipients include a first pharmaceutically acceptable excipient and optionally a second pharmaceutically acceptable excipient;
the first pharmaceutically acceptable excipient comprises said microcrystalline cellulose and at least one selected from a filler and a disintegrant;
said filler is at least one selected from starch, lactose, lactose monohydrate, cellulose-lactose, pregelatinized starch, sucrose, mannitol, sorbitol, calcium phosphate, dextrin, microcrystalline cellulose, calcium hydrogen phosphate and mannitol-starch complex;
said disintegrant is at least one selected from croscarmellose sodium, calcium carboxymethyl cellulose, sodium carboxymethyl starch, methyl cellulose, low-substituted hydroxypropyl cellulose, crospovidone and chitosan; and
the second pharmaceutically acceptable excipient is at least one selected from lubricant, wetting agent, auxiliary lipid, glidant, sweetener, flavoring agent, solvent, cosolvent, suspending agent, isotonic agent, buffers, preservative, antioxidant, colorant, and foaming agent.

9. The pharmaceutical preparation of claim 8, wherein said lubricant is at least one selected from magnesium stearate, colloidal silica, talc, sodium lauryl sulfate, calcium stearate, polyethylene glycol 4000, polyethylene glycol 6000, sodium stearyl fumarate, glyceryl monostearate and hydrogenated vegetable oil.

10. The pharmaceutical preparation of claim 1, wherein, in parts by weight, said pharmaceutical preparation comprises:
5 to 40 parts by weight of the first active component,
5 to 40 parts by weight of the second active component,
30 to 70 parts by weight of a filler,
8 to 20 parts by weight of a disintegrant,
0.5 to 5 parts by weight of a lubricant.

11. The pharmaceutical preparation of claim 1, wherein said first active component and said second active component are at a weight ratio of (0.5-3):1.

* * * * *